(12) United States Patent
Aghazadeh et al.

(10) Patent No.: US 11,191,334 B2
(45) Date of Patent: Dec. 7, 2021

(54) STERILE ENCLOSURE FOR A HAND-HELD ELECTRONIC DEVICE AND METHODS OF USING THEREOF

(71) Applicant: MDM Medical LLC, Boston, MA (US)

(72) Inventors: Mehran S Aghazadeh, Newton, MA (US); Daniel Michael Ward, Wellesley, MA (US); Michael Barenboym, Boston, MA (US)

(73) Assignee: MDM Medical LLC, Boston, MA (US)

( * ) Notice: Subject to any disclaimer, the term of this patent is extended or adjusted under 35 U.S.C. 154(b) by 661 days.

(21) Appl. No.: 16/107,955

(22) Filed: Aug. 21, 2018

(65) Prior Publication Data

US 2020/0060401 A1 Feb. 27, 2020

(51) Int. Cl.
*A45C 11/00* (2006.01)
*H04B 1/3888* (2015.01)
*A61B 50/00* (2016.01)

(52) U.S. Cl.
CPC ............ *A45C 11/00* (2013.01); *H04B 1/3888* (2013.01); *A45C 2011/002* (2013.01); *A45C 2011/003* (2013.01); *A61B 50/00* (2016.02)

(58) Field of Classification Search
CPC .............. A45C 11/00; A45C 2011/002; A45C 2011/003; A61B 50/00; H04B 1/3888
USPC ...................................................... 220/367.1
See application file for complete search history.

(56) References Cited

U.S. PATENT DOCUMENTS

| | | | |
|---|---|---|---|
| 5,944,432 A | 8/1999 | Richards | |
| 6,132,367 A | 10/2000 | Adair | |
| 8,964,405 B2 * | 2/2015 | La Porte | A61L 2/10 361/807 |
| 9,317,076 B2 | 4/2016 | Rayner | |
| 9,550,620 B2 | 1/2017 | Naor | |
| 9,615,476 B2 | 4/2017 | Rayner | |
| 2006/0274493 A1 * | 12/2006 | Richardson | H05K 5/068 361/679.4 |
| 2010/0096963 A1 * | 4/2010 | McLaughlin | A61B 46/10 312/223.1 |
| 2011/0279383 A1 * | 11/2011 | Wilson | G06F 3/0412 345/173 |
| 2013/0186798 A1 * | 7/2013 | Naor | A45C 11/00 206/524.3 |
| 2013/0334071 A1 * | 12/2013 | Carnevali | G06F 1/1628 206/37 |
| 2016/0264275 A1 * | 9/2016 | Baker | A61L 2/00 |
| 2017/0035166 A1 * | 2/2017 | Zondervan | A45C 11/00 |
| 2017/0035170 A1 | 2/2017 | Rayner | |
| 2017/0045920 A1 | 2/2017 | Armstrong | |
| 2017/0085287 A1 | 3/2017 | Naor | |
| 2017/0099372 A1 | 4/2017 | Chen | |
| 2018/0234127 A1 * | 8/2018 | Lambert | A45C 11/00 |

(Continued)

*Primary Examiner* — J. Gregory Pickett
*Assistant Examiner* — Niki M Eloshway
(74) *Attorney, Agent, or Firm* — Boris Leschinsky

(57) ABSTRACT

A sterile enclosure to bring a non-sterile hand-held electronic device such as a smartphone or a tablet into a sterile field comprises a rigid frame, a rigid base and a device holder configured to accept the hand-held device thereon. The use of the device holder to contain the hand-held device prior to engaging with the base and positioning the device therein, allows avoiding contamination of sterile components during use. A sterility indicator is also provided to continuously monitor the sterile enclosure for a possible breach in sterility while inside the sterile field.

6 Claims, 13 Drawing Sheets

(56) References Cited

U.S. PATENT DOCUMENTS

| | | | |
|---|---|---|---|
| 2019/0047815 A1* | 2/2019 | Kim | G06F 1/1626 |
| 2020/0069015 A1* | 3/2020 | Poon | A45C 13/008 |
| 2020/0265825 A1* | 8/2020 | Fong | G10L 25/51 |
| 2020/0288833 A1* | 9/2020 | Fathollahi | A45C 11/00 |

* cited by examiner

STERILE ENCLOSURE FOR A HAND-HELD ELECTRONIC DEVICE AND METHODS OF USING THEREOF

BACKGROUND OF THE INVENTION

The present invention relates to a device for providing a sterile enclosure for a non-sterile hand-held mobile electronic device such as a smartphone or a tablet. In particular, the invention relates to a sterile cover having an optional sterility indicator and configured to bring the mobile electronic device within a sterile operating field.

Maintaining sterility within an operating field is critical for preventing infection. Traditionally, disposable supplies and instruments were used along with sterilized reusable equipment. Proliferation of small electronic devices such as mobile phones and computer tablets has made it attractive to utilize their capabilities in the operating room. In particular, hand-held smartphones and tablets can be used to access patient records, record photographs and videos, dictate notes etc. More recently, they have been used either as a surgical equipment or for operating a surgical equipment. However, like all other surgical instruments, these devices cannot be brought into the operating field unless they are sterile. Most conventional methods of sterilization such as autoclaving or exposure to fluid or gas sterilization compounds are not suitable for such devices due to the risk of damage and time required for sterilization.

One solution to this problem is to use a disposable sterile cover configured to surround the entire hand-held electronic device such that no non-sterile portion of the device is exposed to the outside. Many devices of the prior art describe such generic sterile covers ranging from soft plastic bags to hard plastic clam-shell devices. Examples of such devices can be found in U.S. Pat. Nos. 6,132,367, 9,317,076, 9,615,476 as well as US Patent Application Nos. 2013/0186798, and 2017/0085287.

Although prior art devices can provide the basic function of surrounding the small hand-held device with a sterile cover, they lack in many important aspects. First, they do not provide for a convenient and secure method of placing the device into a sterile cover. Such process usually involves cooperation of a first person in a non-sterile field and a second person in a sterile field. Generally speaking, a sterile cover is made to match the size of the hand-held device. Any errors in moving a non-sterile hand-held electronic device by a first person into a sterile cover held by a second person may result in touching of the sterile part by a non-sterile device or a person causing a loss of sterility of the cover rendering it useless.

Second, once the device is placed into the sterile field, there is no way to tell whether the cover may be compromised and sterility may be lost—as the operating field is full of sharp instruments and objects that can inadvertently penetrate the sterile cover of the mobile device leading to loss of sterility.

The need exists therefore for an improved sterile cover for a mobile electronic device that can assure initial and continuous sterility of the mobile device while in the operating field.

SUMMARY OF THE INVENTION

Accordingly, it is an object of the present invention to overcome these and other drawbacks of the prior art by providing a novel sterile enclosure for a hand-held electronic device configured to assure sterility upon placement of the device therein as well as throughout its use.

It is another object of the present invention to provide a novel sterile enclosure for a hand-held electronic device configured to facilitate a simple process of placement of the device within the enclosure while assuring no loss of sterility during this process.

It is a further object of the present invention to provide a novel sterile enclosure for a hand-held electronic device which provides a continuous visual indicator of maintaining sterility so that the user can have a piece of mind that the device and its enclosure would not jeopardize the sterility of the operating field.

It is yet a further object of the present invention to provide a novel sterile enclosure for a hand-held electronic device capable of allowing the user to operate the device while within the sterile enclosure.

It is a further yet object of the present invention to provide a novel sterile enclosure for a hand-held device capable of retaining the device inside thereof in a fixed position so as to make it convenient to operate the device through the top portion of the sterile enclosure.

It is yet a further object of the present invention to provide a novel sterile enclosure allowing wired and wireless communication with the hand-held electronic device sealed therein without compromising the sterility of the enclosure. This may be particularly advantageous with operating a small remote control of a large imaging device, such as MRI, CT, X-Ray, ultrasound imaging equipment etc.

The sterile enclosure of the invention includes a base, a frame, and a device holder assembly. Both the frame and the base are configured to enclose a hand-held electronic device. One key novel feature is providing a device holder assembly which facilitates positioning of the device inside the sterile enclosure in a way that assures sterility and coordination between a first person located in a non-sterile field and a second person located in a sterile field using a series of steps described in greater detail below.

A vacuum port is also provided so as to allow air evacuation from the sterile enclosure once the hand-held device is placed inside thereof. Applying vacuum allows to fixedly retain the device inside the sterile enclosure as well as operating the device through a clear flexible window located next to the touch-sensitive screen of the device.

A further aspect of the present invention is providing a continuous sterility indicator to assure the user that the sterility of the enclosure is maintained throughout its use in the sterile field. To achieve this, a collapsible elastic chamber is provided on one side of the sterile enclosure. Evacuation of air causes a shortening of the chamber leading to its protruding bulb to retract under a masking edge of the base of the sterile enclosure. If the enclosure is punctured and the vacuum is lost, the compressible chamber will expand and reveal the protruding bulb—serving as a visual indicator of a breach of sterility.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE PREFERRED EMBODIMENT OF THE INVENTION

Figure 1:
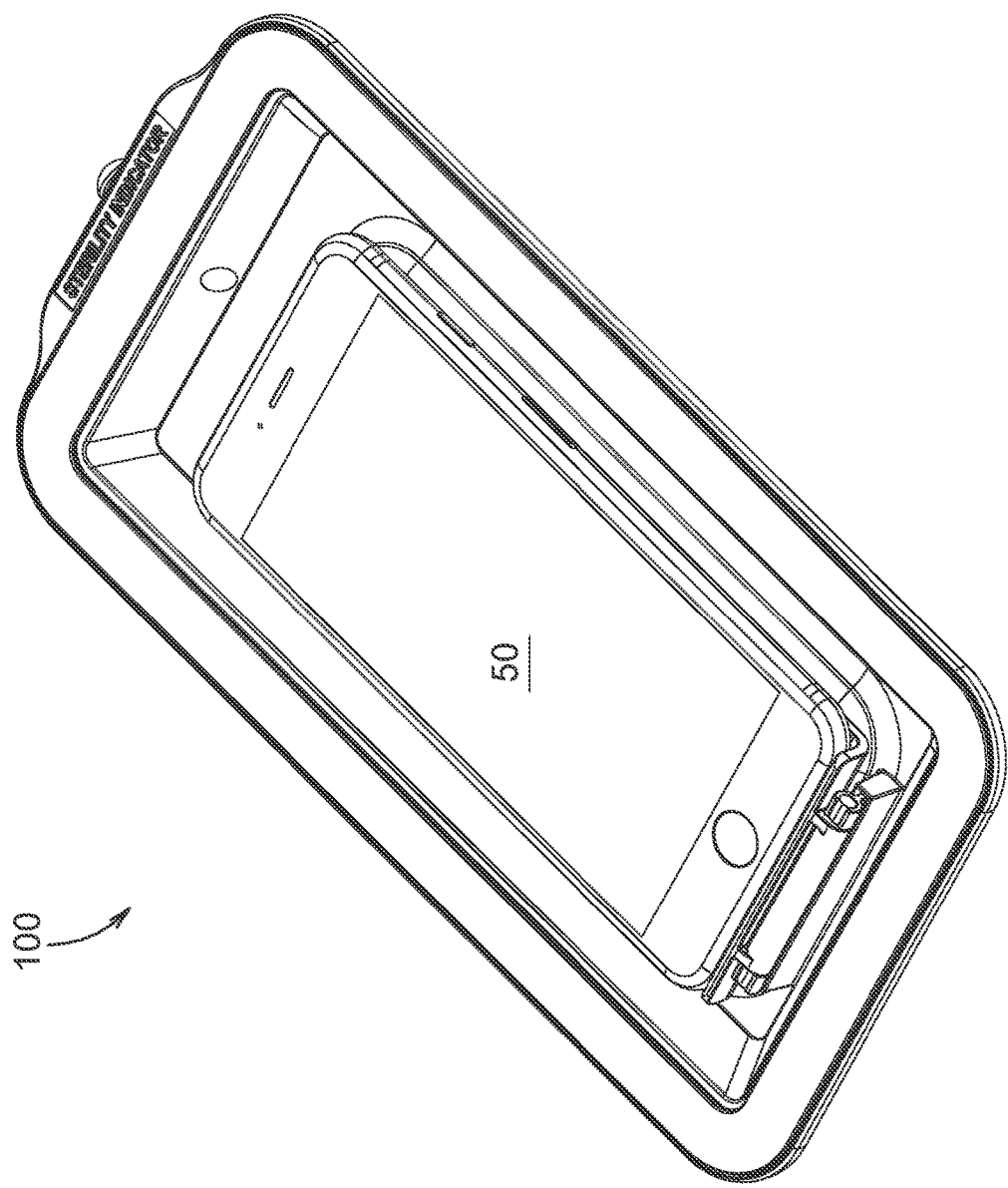
FIG. 1 is a general view of the novel sterile enclosure assembly with a hand-held electronic device inside thereof.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The term "hand-held electronic device" is used herein to describe a variety of small electronic devices such as mobile phones, smartphones, computer laptops, notebooks and tablets, PDAs, pagers, calculators, voice recorders, digital cameras, remote controls for larger pieces of electronic equipment such as various MRI, CT, X-Ray, ultrasound, and other imaging equipment and alike. Terms "small" and "hand-held" are used herein interchangeably.

Figure 2:
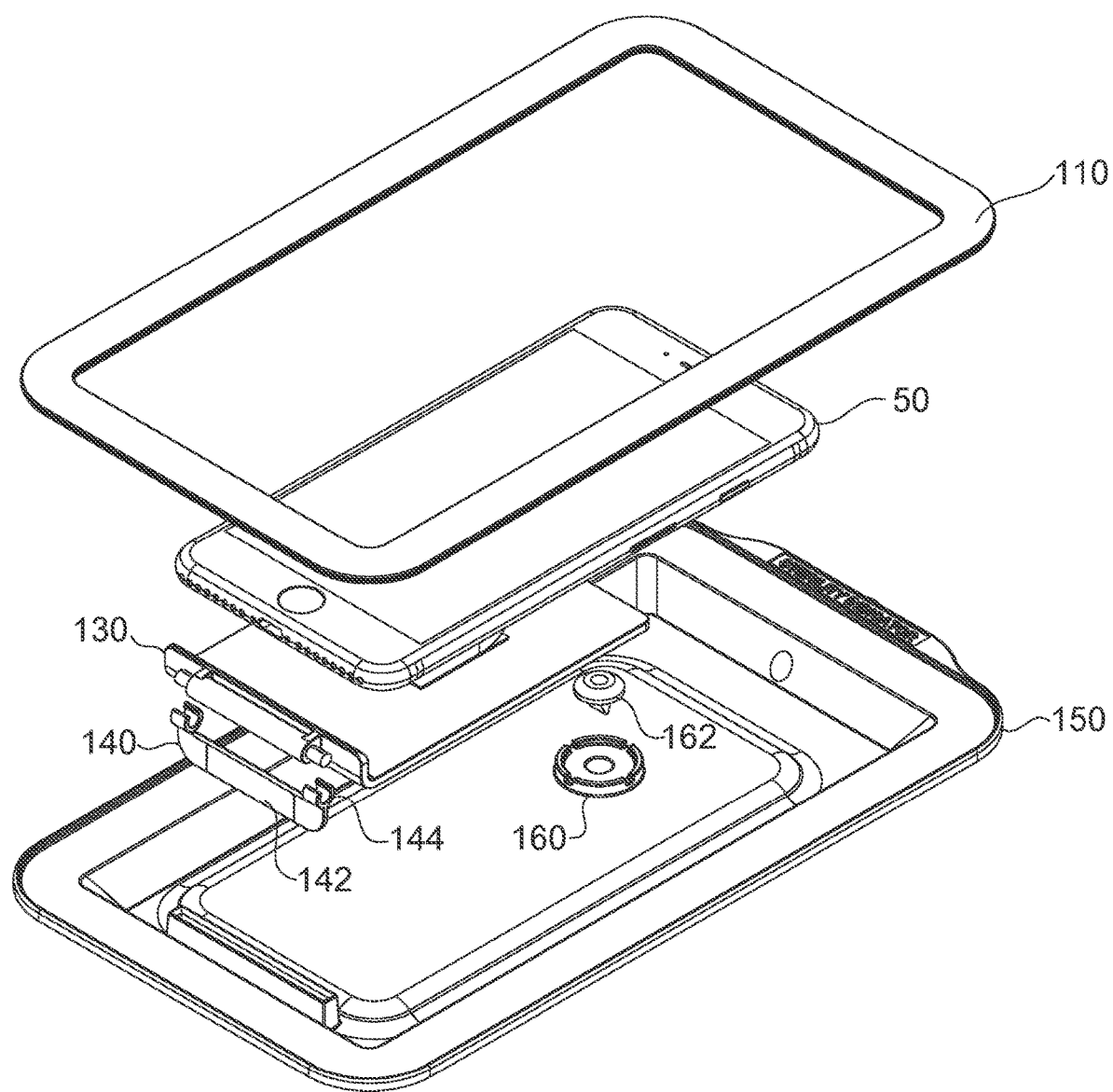
FIG. 2 is an exploded view of the same.

FIG. 1 shows a general view and FIG. 2 shows an exploded view of the sterile enclosure of the invention 100 containing a hand-held device 50. In broad terms, the sterile enclosure 100 may be assembled using a base 150, a device holder assembly 130 and 140, and an frame 110, all of these components are now described in greater detail below.

The main component of the sterile enclosure 100 is the rigid base 150, which may be generally made as a tray with a central depression 154 optionally having a device outline receptacle 156 made with a width, length and depth suitable to contain the hand-held device 50. In embodiments, the length of the device receptacle 156 may vary from about 3 inches to about 14 inches, such as 3 inches, 4 inches, 5 inches, 6 inches, 7 inches, 8 inches, 9 inches, 10 inches, 11 inches, 12 inches, 13 inches, 14 inches or any dimension inbetween. The width of the device receptacle 156 may vary from about 2 inches to about 10 inches, such as 2 inches, 3 inches, 4 inches, 5 inches, 6 inches, 7 inches, 8 inches, 9 inches, 10 inches or any dimension inbetween. The depth of the device receptacle location as measured from the ledge 152 may be from about 0.3 inches to about 1 inch. In embodiments, the depth may be 0.3 inches, 0.4 inches, 0.5 inches, 0.6 inches, 0.7 inches, 0.8 inches, 0.9 inches, 1 inch or any suitable dimension inbetween as the present invention in not limited in this regard.

Figures 3A, 3B:
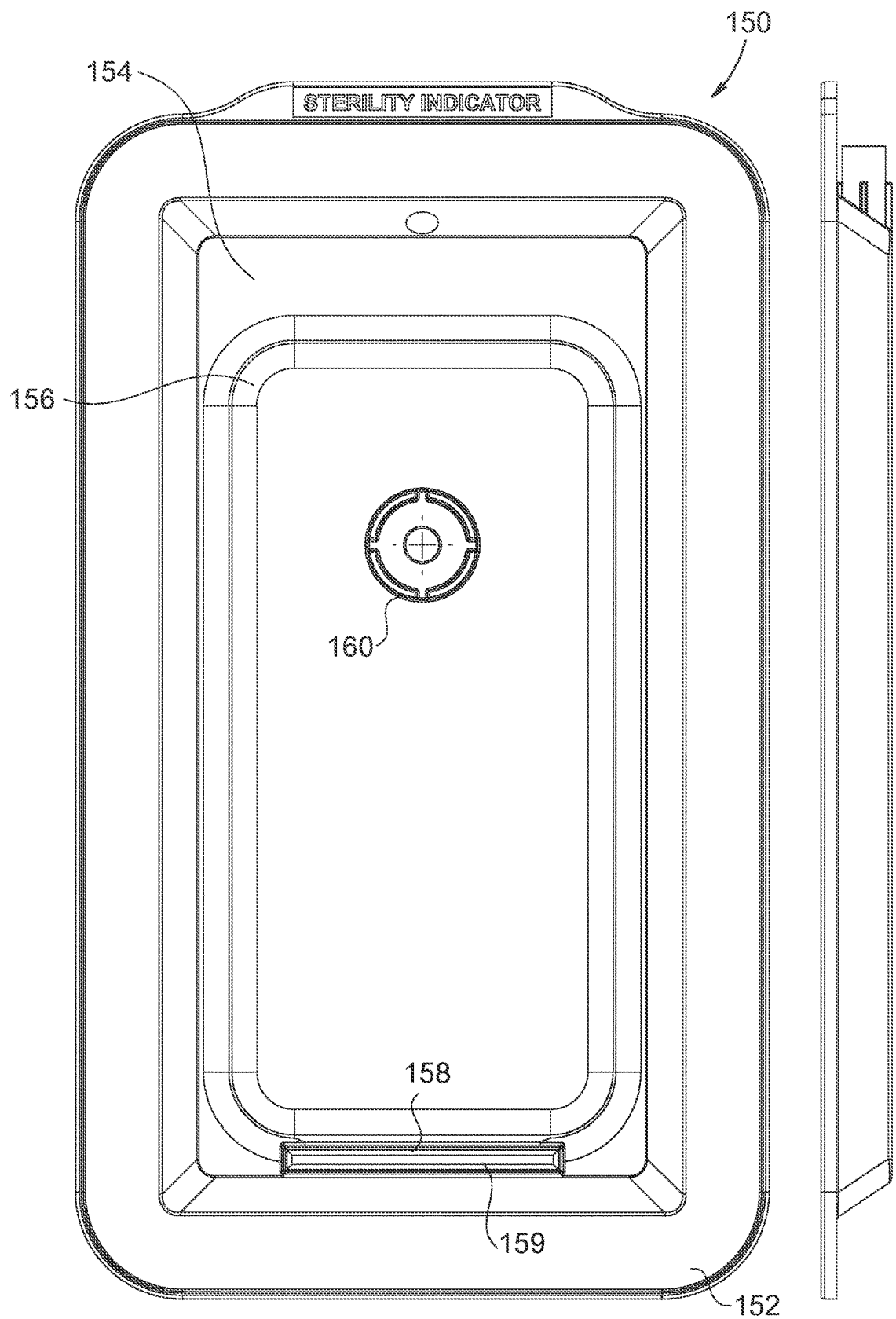
FIG. 3a is a top view of the base.
FIG. 3b is the side vide of the same.

The base 150 may also contain a device receptacle 158 shaped to accept the device holder 130 therein—see FIGS. 3a and 3b. The base 150 may be made with an outer lower sealing ledge 152 configured to sealingly mate with a respective upper sealing ledge 116 of the frame 110 (see FIG. 5a) in an airtight manner. This may be accomplished for example by providing an adhesive layer on top of either one or both the lower sealing ledge 152 and the upper sealing ledge 116. Each one or two adhesive layers may be protected with a removable masking tape or paper. Removal of the masking tape and bringing the lower sealing ledge 152 and the upper sealing ledge 116 together during the assembly of the sterile enclosure 100 will provide an airtight permanent or separable attachment between the base 150 and the frame 110 of the sterile enclosure 100.

In alternative embodiments, the lower sealing ledge 152 may have a groove and the upper sealing ledge 116 may have a tongue feature sized to mate and clamp together in an airtight manner during the assembly process.

In further embodiments, the airtight assembly of the upper sealing ledge 116 and the lower sealing ledge 152 may be accomplished using other arrangements such as placing a tape around their perimeter, heating the edges to fuse them together and others, as the invention is not limited in this regard.

In further yet embodiments, the base 150 may be hingedly attached to the frame 110 on one side (not shown) using for example a living hinge design allowing both shells 150 and 110 to close together and bring the lower sealing ledge 152 next to the upper sealing ledge 116.

The base 150 may further contain an air evacuation port, which may be designed using a one-way valve 162 positioned in the valve receptacle 160 using for example a press-fit assembly. Valve receptacle 160 may be manufactured together with the rest of the base 150 as a single piece, using any known manufacturing techniques such as molding, thermoforming, dip-coating, 3D printing etc. an optional connector may also be provided (not shown) to attach the base 150 to a vacuum source so as to evacuate air therefrom.

The entire base 150 may be made using a suitable rigid polymer material such as polycarbonate for example, which can be sterilized without a risk of changing its shape using conventional sterilization techniques as described below. In embodiments, the base 150 may be made using a rigid transparent polymer so that even while inside the sterile enclosure 100, a rear camera of the hand-held device 50 may still be used. In embodiments, the location of the air evacuation port may be selected to not obstruct the view of the rear camera of the device 50 so as not to interfere with a potential use thereof.

The base 150 may further contain a device receptacle 158 configured to have a groove 159 or another suitable design feature to accept the corresponding stabilizer 142 of the device connector 140 as described in greater detail below.

The base 150 may further contain a sterility indicator 170 assembly comprising the masking edge 176 and the compressible elastic chamber 171 described below and illustrated in FIGS. 8 to 12—which is now described in greater detail below.

Figure 8:
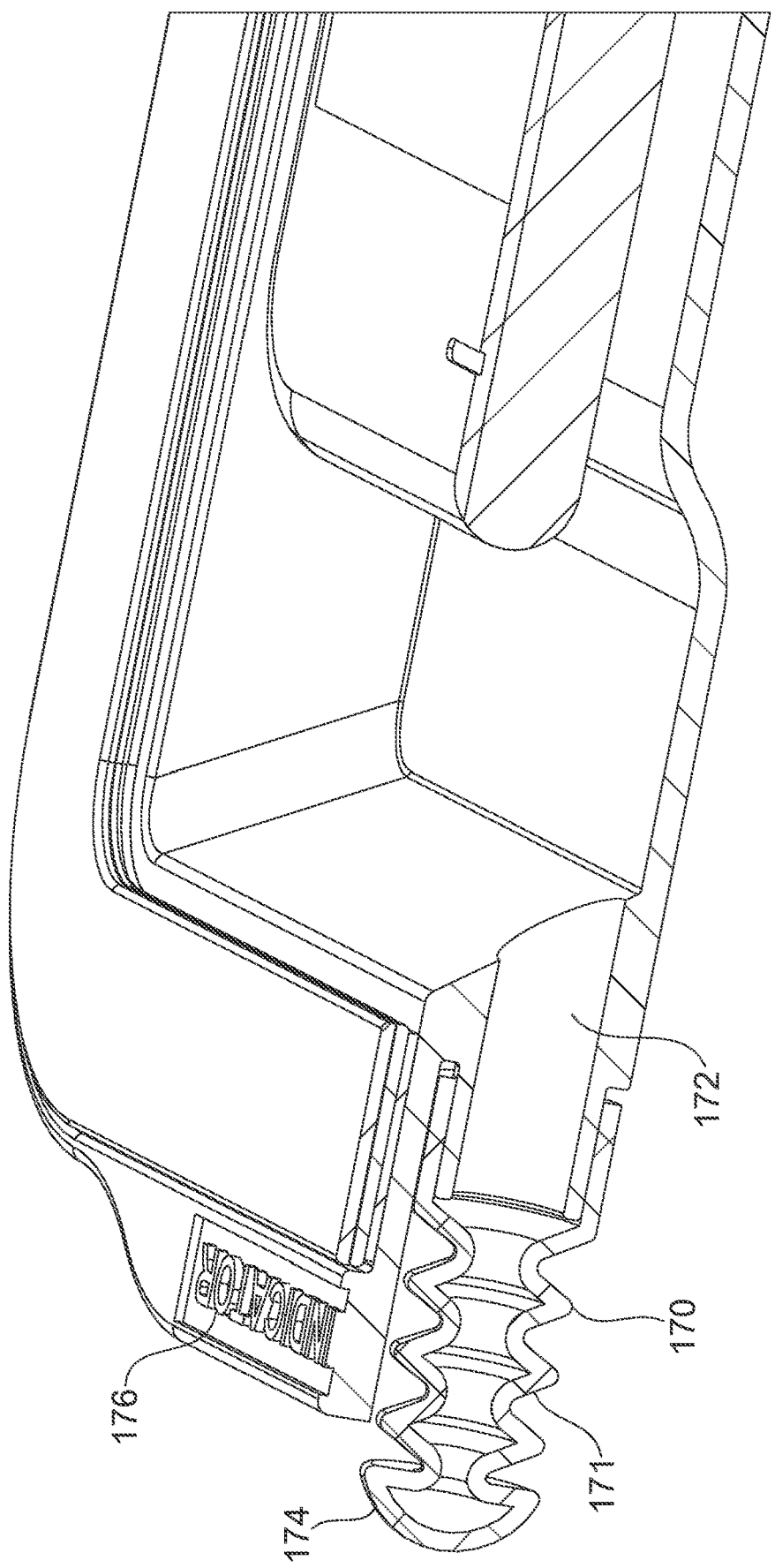
FIG. 8 shows a close-up cross-sectional view of the base illustrating sterility indicator built therein.

As seen in FIG. 8, an exemplary sterility indicator may include a collapsible elastic chamber 171 attached to an opening 172 in the base 150. The elastic chamber 171 may be made from a corrugated bellows-type elastic material such as rubber, silicone, or an elastic polymer terminating with a bulb 174 forming a dead-end of the chamber 171. The bulb may be positioned to protrude beyond the masking edge 176 defining an exposed position thereof prior to use of the sterile enclosure. In embodiments, the bulb 174 may be made from a bright colored material such as bright red or bright yellow such that its visible appearance may be perceived as a warning sign. As opposed to being concealed by a masking edge 176, in other embodiments of the invention the bulb 174 may be contained within a well hiding the collapsible chamber 171. The extent of compressibility of the chamber 171 may be selected such that applying vacuum to the inside of the chamber may cause it to collapse and shorten in a longitudinal direction so as to move the bulb 174 away from view and behind the masking edge 176, defining a hidden position of said collapsible chamber 171.

Figure 3C:
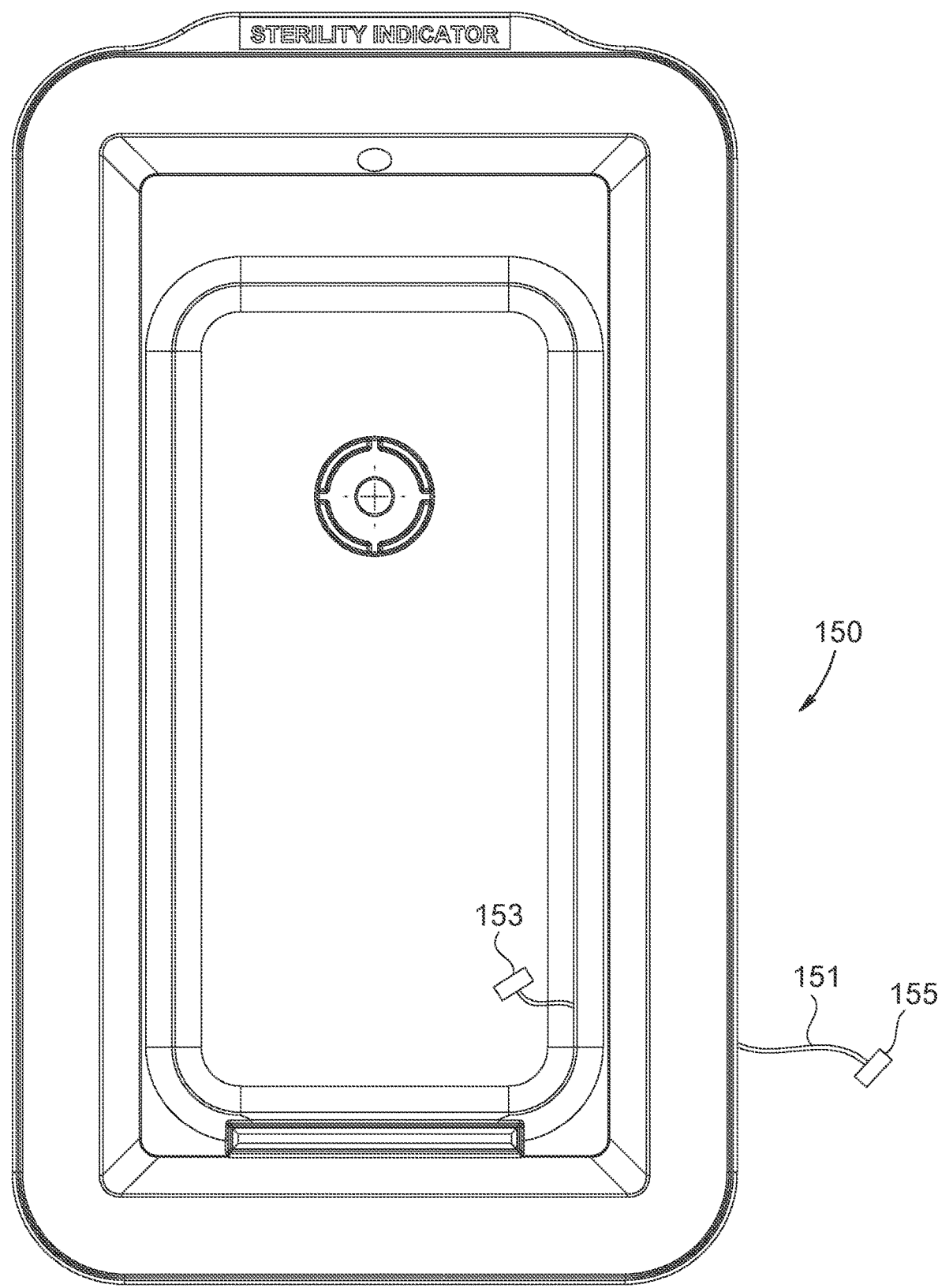
FIG. 3c is a top view of an alternative design of the base containing an electrical conduit sealingly routed therethrough.

In embodiments, an electrical conduit 151 may be incorporated with or sealingly inserted inside and routed through the base 150—see FIG. 3c. Such electrical conduit 151 may be sealed internally along its length so as to prevent air from escaping from to coming into the inside space of the sterile enclosure 100. The electrical conduit 151 may contain one or more electrical connectors and may be equipped with an inner electrical connector 153 selected to be operably attached to one or more electrical connectors associated with the plug-in port of the hand-held device 50. The other external portion of the conduit 151 may be terminated with a respective outer electrical connector 155 which may be designed to mimic the corresponding electrical port connectors on the hand-held device 50. In this case, the conduit 151 may serve as an electrical extension for the hand-held device 50 to utilize its electrical connections outside of the boundaries of the sterile enclosure 100.

Figures 4A, 4B:
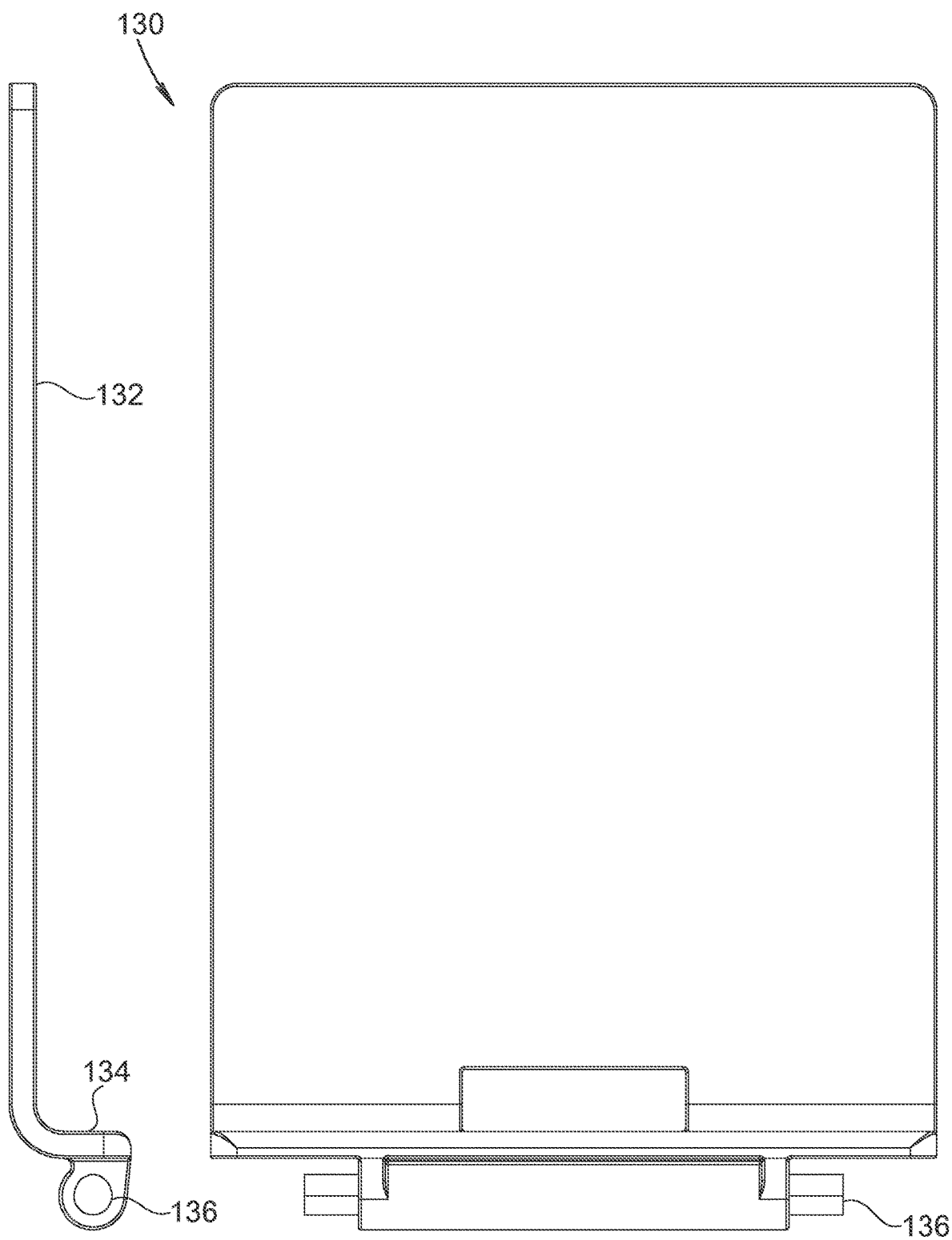
FIG. 4a is a side view of the device holder.
FIG. 4b is a top view of the same.

To facilitate device placement inside the sterile enclosure 100 without compromising the field of sterility, there may be provided a device holder 130—as seen in FIGS. 4a and 4b. The prior art sterile covers describe the hand-held device as simply being placed in the space between the upper and the base. This procedure carries a high risk of contamination by a first non-sterile person holding the non-sterile hand-held device by inadvertent touching of the portions of the sterile covers typically held by a hand of a second sterile person within the sterile field. Coordination of movements between the first and the second person has to be precise in order to position the device in the sterile cover without touching anything else in the sterile field. While certainly being possible to do so, this process carries a high risk of contamination when a simple wrong movement puts the sterility of the field in jeopardy.

The device holder assembly 130 of the present invention is intended to serve as an intermediate component which is used to temporarily retain the hand-held device while placing it inside the space defined by the two shells of the sterile cover. In embodiments, the device holder assembly 130 may be designed as an L-shaped holder 132 equipped with a retaining ledge 134. A generally flat back portion of the holder 132 may be sized to cover some, all, or at least a substantial portion of the hand-held device 50, which may be rested on the ledge 134 and leaned against the holder 132. In embodiments, the holder 132 may be made using a transparent material or optionally contain a window opening located next to the back camera of the hand-held device 50 so as to not obstruct the rear-view video capture using the hand-held device if desired.

The lower ledge 134 may be further equipped with the central axis 136 forming part of a hinge configured to allow rotation of the device holder 132 about thereof for the purposes of lowering thereof into the depression space of the base 150—as will be explained in greater detail below. Alternative designs to accomplish this rotation may be used in place of the axis 136 such as a living hinge (not shown) as the present invention is not limited in this regard.

The device holder assembly 130 may be designed to be assembled with the connector 140, for example using a snap-fit method of rotatably fitting these two components together—see FIG. 2. The connector 140 may have two forks 144 configured to snap fit around the axis 136 for that purpose. Alternative designs to accomplish the same objective may be apparent to those skilled in the art as the invention is not limited in this regard. The connector 140 may have an engagement portion for attaching thereof to the base. In embodiments, this engagement portion may be a stabilizer 142 which may be provided at the lower end of the connector 140 and sized to fit inside the groove 159 of the base 150.

Figures 5A, 5B:
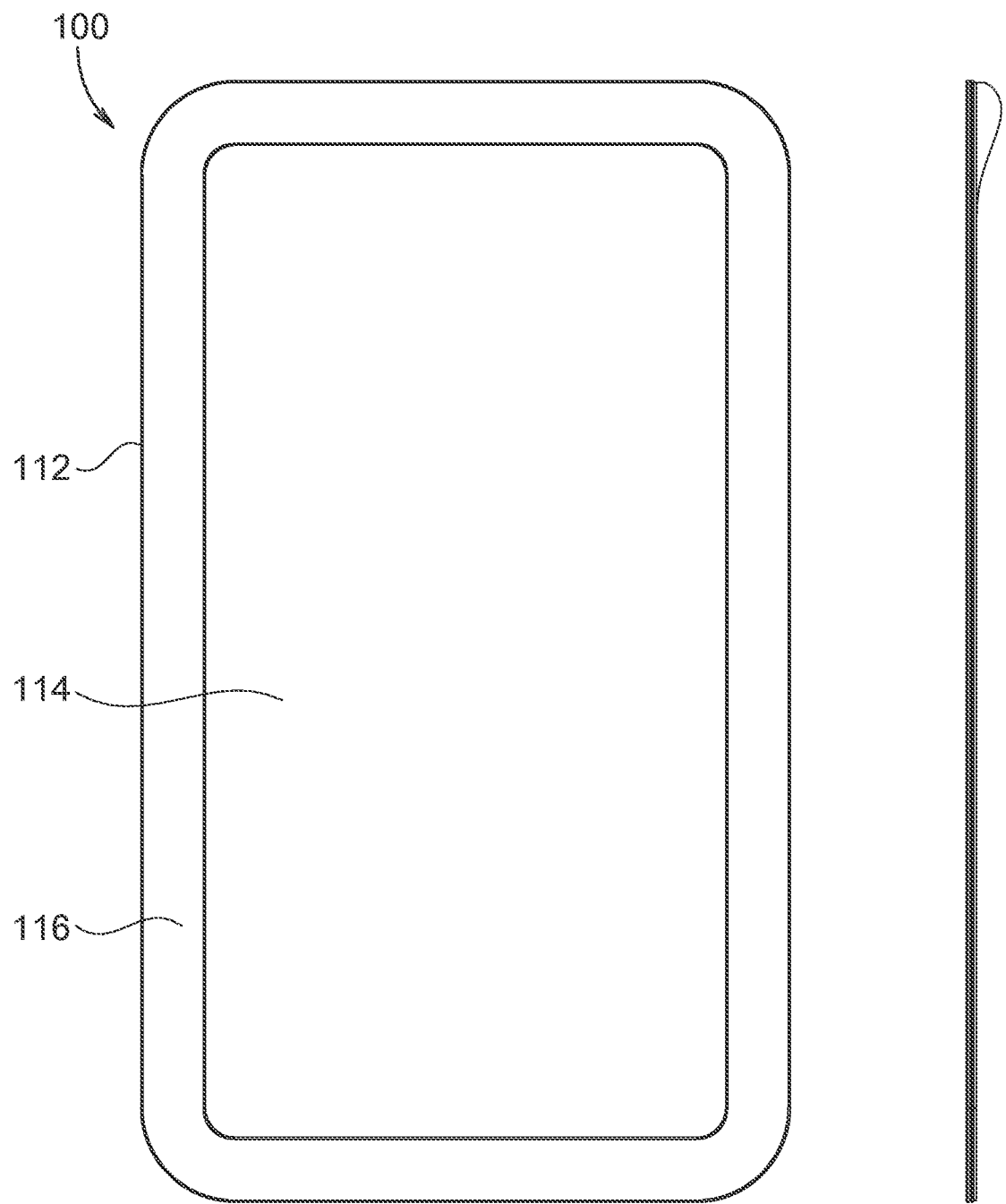
FIG. 5a is a top view of the frame.
FIG. 5b is a side view of the same.

The last component of a three-piece assembly of the sterile enclosure of the present invention is the frame 110 seen in FIGS. 5a and 5b. The frame 110 may comprise a generally flat and rigid rectangular border 112 having an upper sealing ledge 116 sized and designed to correspond to the lower sealing ledge 152 of the base 150—so as to form an airtight seal inbetween after the sterile enclosure of the present invention is fully assembled. A flexible transparent window 114 may be located in the central portion of the border 112 and configured to allow operation of the hand-held device 50 therethrough—in a manner similar to screen protectors for cellular phones.

In embodiments, rigid components of the sterile enclosure of the present invention may be made of a lightweight material that can be sterilized, such as plastic, carbon fiber, metal, alloys, ceramics, composites, or glass, among others. Exemplary plastics may include polyethylene, polycarbonate, polypropylene, polyurethane, etc. The flexible transparent window may be made of sterilizable transparent flexible materials, such as thin layer of glass, plastic, polyethylene films (low density polyethylene or linear low density polyethylene), polypropylene, vinyl, or other transparent films. The components of the sterile enclosure 100 may be sterilized via chemical means, X-rays, gamma rays, heat, high pressure or UV light, among others. Chemical sterilization may be accomplished via a solution of ethylene oxide, nitrogen dioxide gas, ozone, hydrogen peroxide, or glutaraldehyde and formaldehyde solution, among others as the present invention is not limited in this regard.

The use of the sterile enclosure 100 is intended to occur in clinical environment where sterilization is required, such as surgery rooms, emergency rooms, hospital rooms, or ambulances, among others. The non-sterilized hand-held electronic device may be operated through the sterilized enclosure device within the sterilized operation area without exposing the patients to potential pathogens that may be present on the non-sterilized mobile device. The cost of operating the non-sterilized surgical devices, such as a C-ARM, a portable X-ray machine and devices used for Computer Assisted Surgery, may be reduced because they can be operated from within the operating room by the attending physician and they don't require additional staff that would otherwise be needed in the operating room to solely operate them. This will also reduce the risk infection introduced by presence of additional people in operating rooms. As shown in the literature, the risk of infection is directly related to a number of people present in the operating room during the surgical procedures.

Prior to using the sterile enclosure 100, it is presumed that all the components thereof may be enclosed in a sterile pouch and sterilized using any of the suitable sterilization methods as described above. A second person located within the sterile field may take the components of the sterile enclosure 100 from the sterile pouch and position them on the sterile table. As a first preparatory step, the connector 140 may be snapped onto the device holder 130 in order to prepare thereof for receipt of the non-sterile hand-held electronic device 50.

Figure 6:
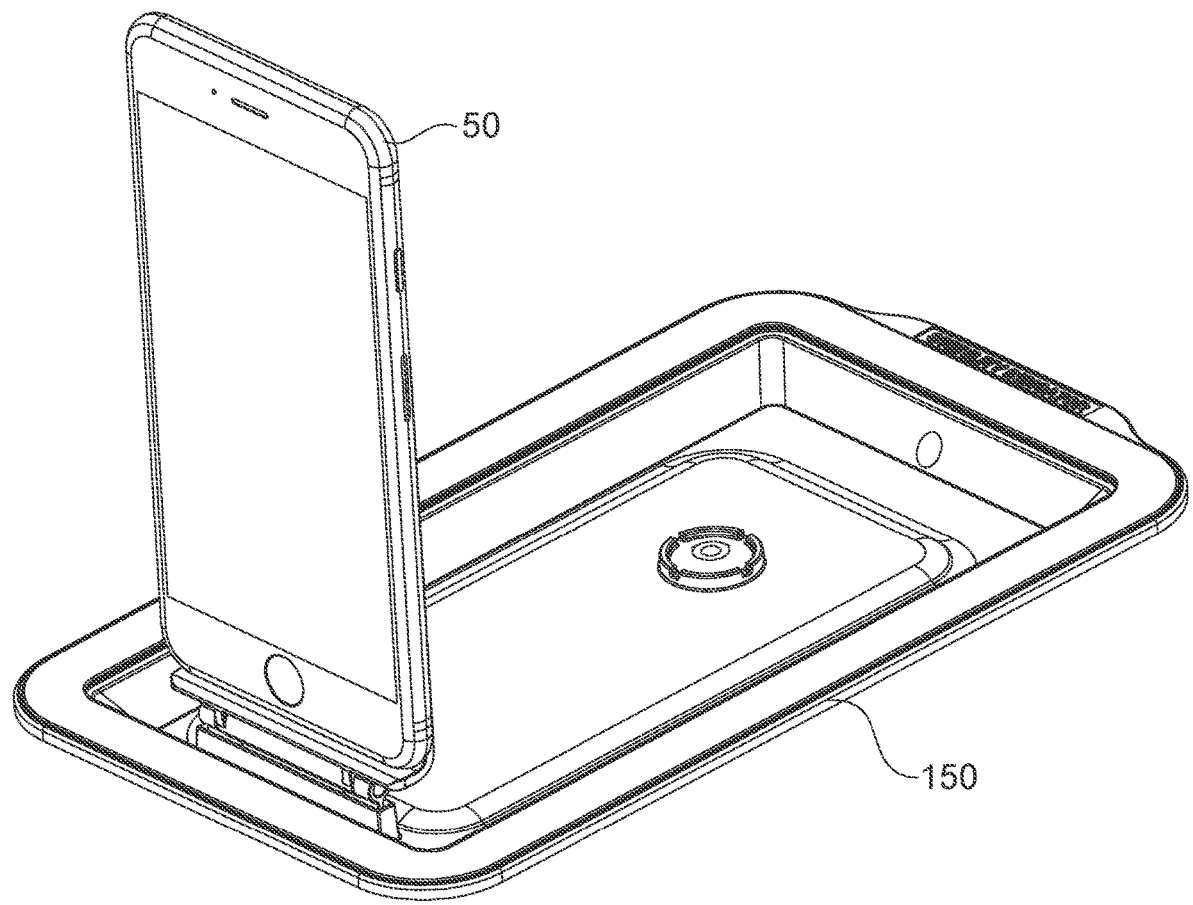
FIG. 6 shows a hand-held device during the process of loading into the sterile enclosure of the invention.
Figure 7:
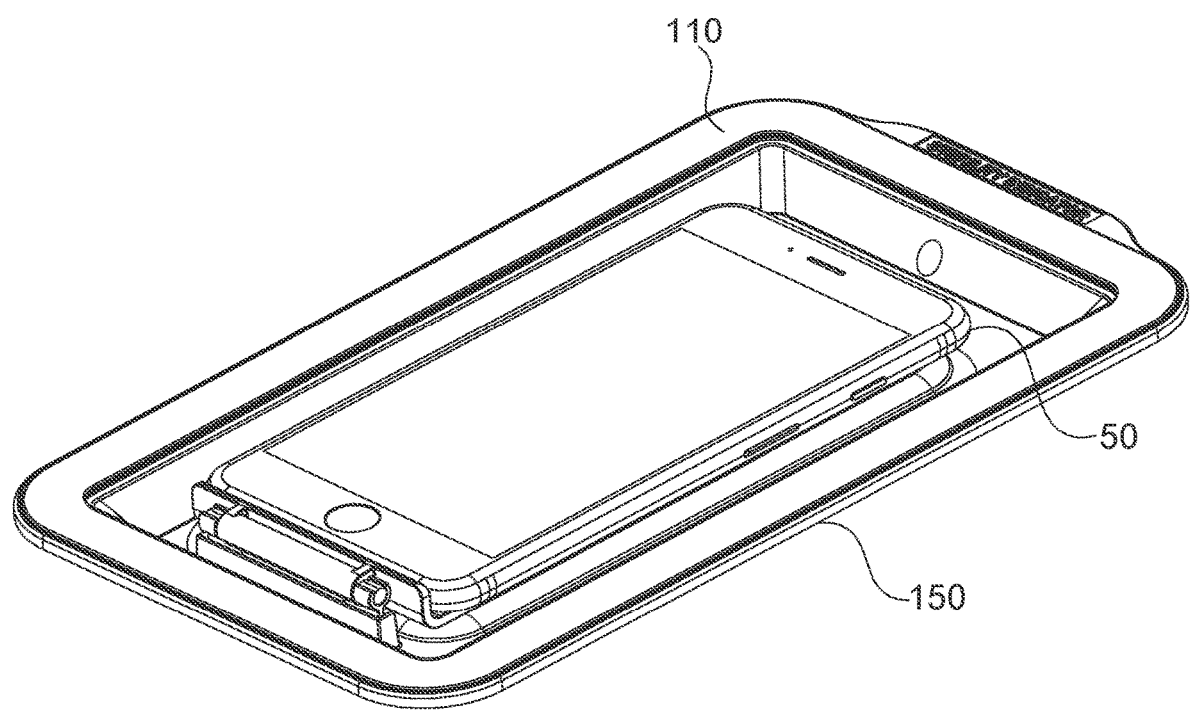
FIG. 7 is the same at a later stage of the process.

In the next step, a first non-sterile person may take a device holder assembly 130/140 and position the device 50 onto thereof so as to rest the bottom edge of the device 50 on the ledge 134 and leaning the back of the device 50 next to the back portion of the device holder 132. Holding both the device 50 and the device holder 130 together, the first non-sterile person may then engage the stabilizer 142 with the groove 159 of the base 150—as seen in FIG. 6. The base 150 may be held by a second sterile person in the sterile field in a generally horizontal orientation. Importantly, the motion of engagement of the stabilizer 142 and the groove 159 together is a simple and easily repeatable act, which may be done without jeopardizing the sterility of the entire sterile field.

Following placement of the device holder 130 and the device 50 onto the end of the base 150 in a generally vertical orientation, a second motion may be performed by the first non-sterile person, namely tilting the device holder 130 to lower down the device 50 into the base 150. As the device holder 130 is engaged with the base 150 on one end thereof, the motion of lowering the device 50 down is easy to complete and is highly repeatable and deliberate—as guided by the rotation of the device holder 130 about the axis 136 until the device 50 is positioned all the way inside the base 150. At this point, the first non-sterile person releases the device 50 and moves away from the sterile field.

In the next step of the assembly, the frame 110 is placed on top of the base 150, optionally with a prior removal of the masking tape and exposure of the adhesive layer on the ledge 152 or the ledge 116. Placing of the frame 110 over the base 150 completes the initial assembly of the sterile enclosure by sealingly connecting both shells together.

As a final step in the assembly process, vacuum is applied to the internal space of the sterile enclosure—for example via the one-way valve 162. Suitable removable attachment may be provided to attach hospital vacuum line to the valve 162. Applying suction to the inside space of the sterile enclosure 100 removes most air therefrom and urges the flexible window 114 of the frame 110 to enclosure and closely adhere to the top screen and operating buttons of the hand-held device 50. Due to its flexibility and thin size, close positioning of the flexible window 114 on top of the device 50 allows operating thereof through the window 114. Applying vacuum may also be helpful in securing the device 50 inside the sterile enclosure 100 to prevent shifting thereof away from the original position.

Figure 9:
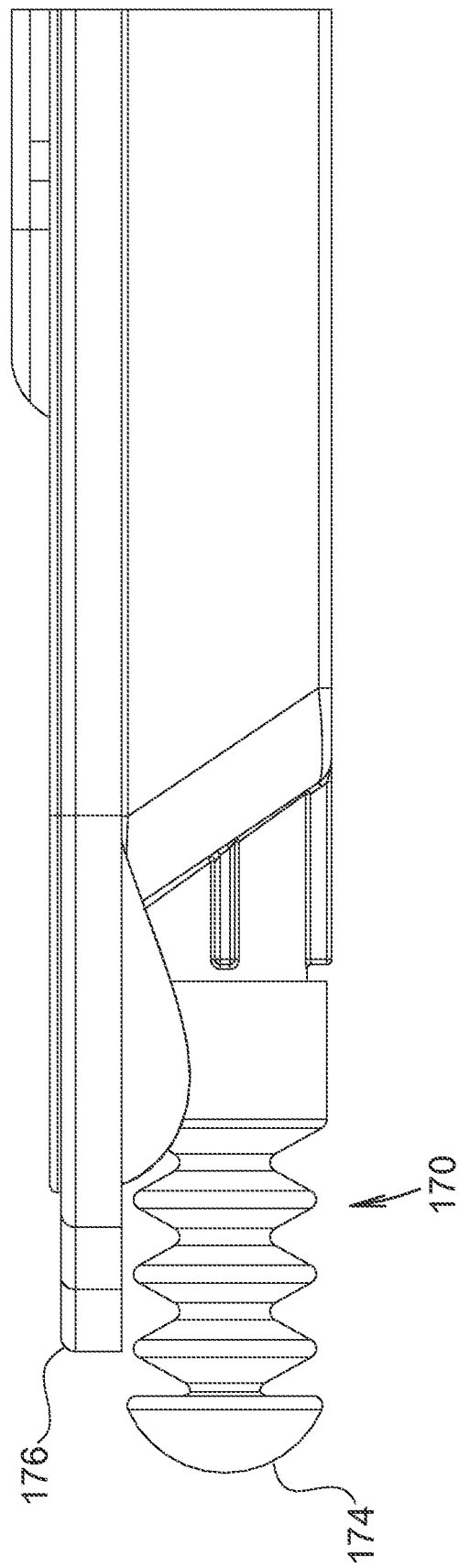
FIG. 9 is a side view of the same in the initial pre-vacuum position.
Figure 10:
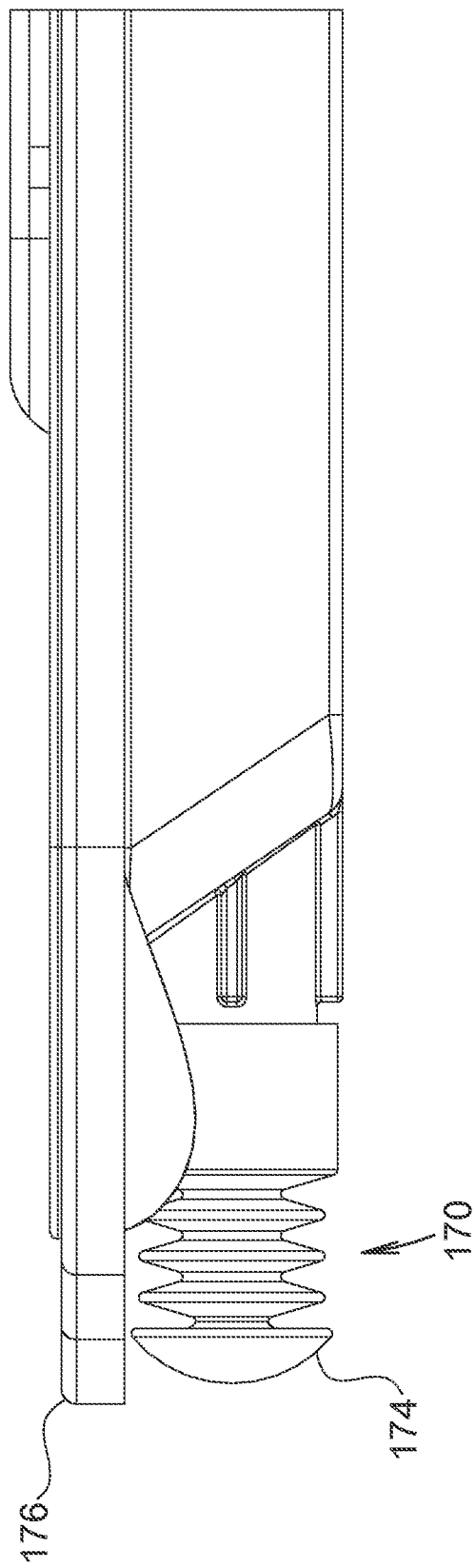
FIG. 10 is a side view of the same after applying vacuum to the sterile enclosure of the invention.
Figure 11:
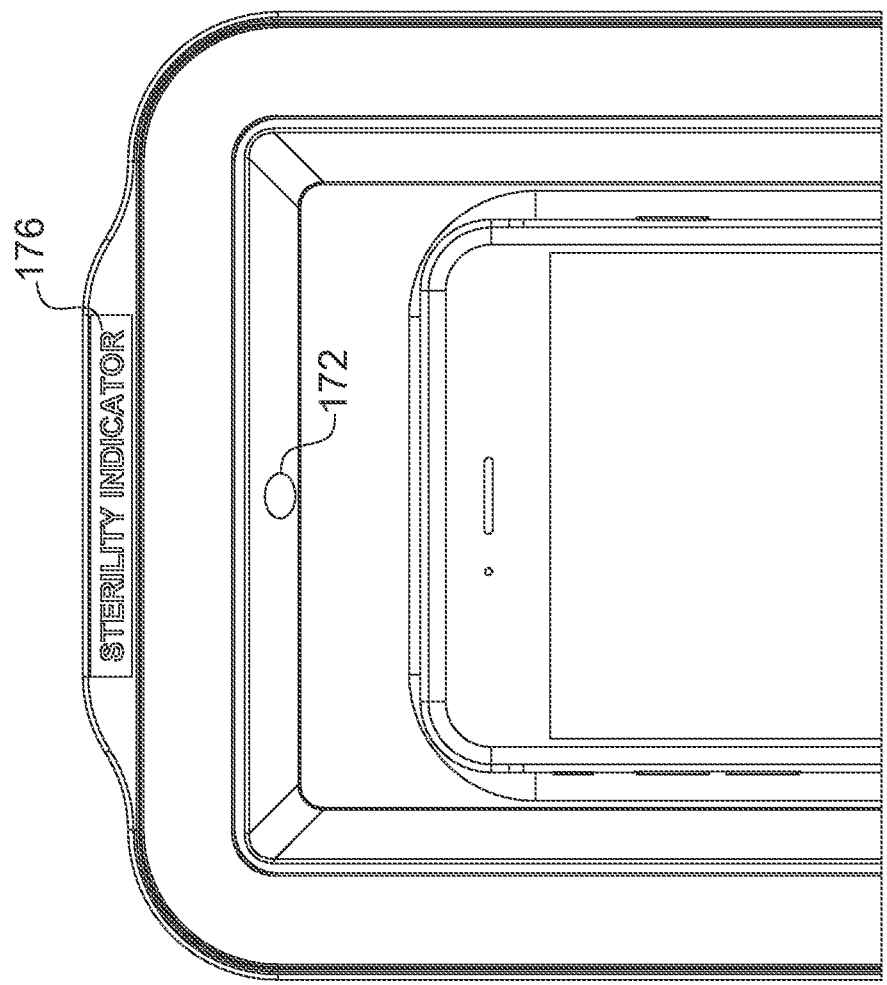
FIG. 11 is a top view of the same as in FIG. 10.
Figure 12:
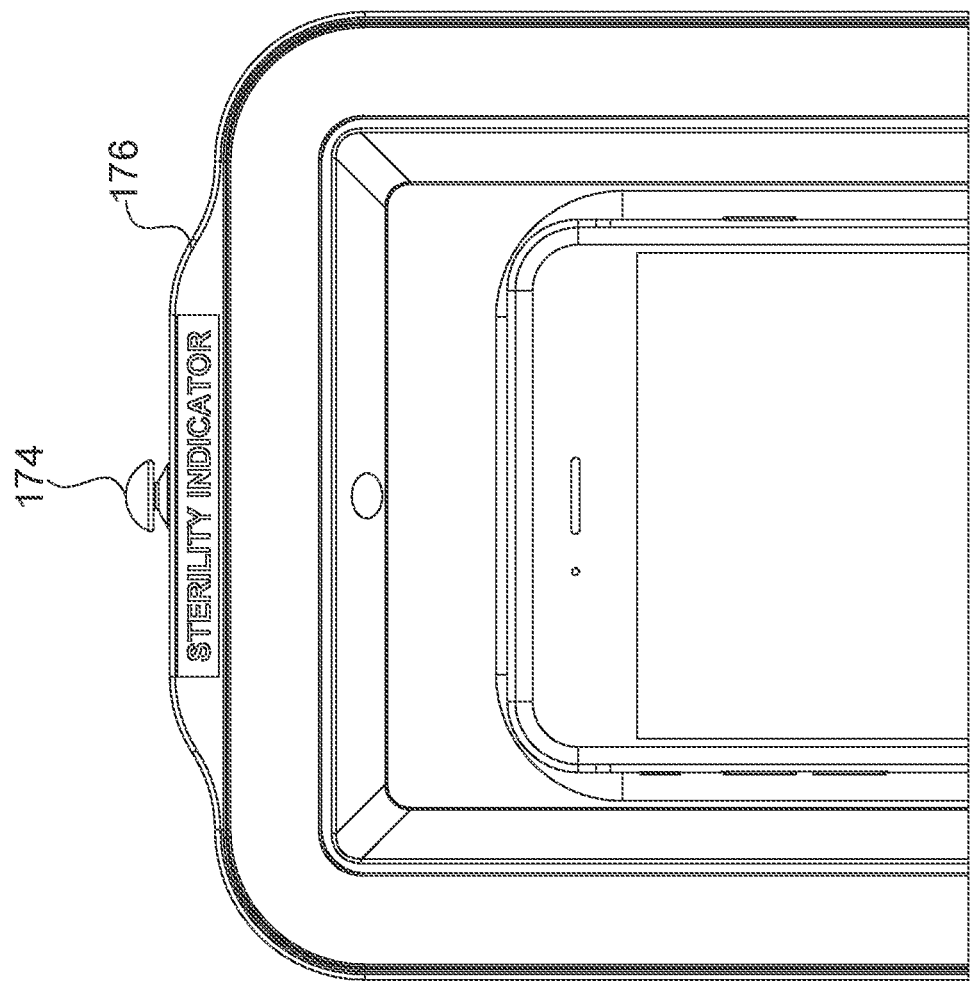
FIG. 12 is a top view of the same as in FIG. 11 with the indicator visible after loss of vacuum and with jeopardized sterility.

While prior to applying suction, the bulb 174 is positioned to be visible from behind the masking edge 176—as seen in FIG. 9, evacuating the air from the inside of the sealed sterile enclosure 100 causes the elastic chamber 170 to collapse and the bulb 174 to move inwards and out of the view as being covered by the masking edge 176—see FIG. 10.

The assembly of the sterile enclosure 100 is now complete and the hand-held device 50 may be brought into the sterile field of the operating room.

During operation of the device 50 within the sterile field, continuous monitoring of the vacuum state of the sterile enclosure 100 may be easily conducted by observing the location of bulb 174—its absence from view (FIG. 11) indicates that the vacuum is maintained. Loss of vacuum (such as resulting from an unexpected nick of the enclosure with a sharp surgical instrument) would cause air leakage into the inside space of the sterile enclosure 100. In turn, that air leakage would urge the expansion of the collapsible chamber 171—leading to the bulb 174 emerging from behind the masking edge 176—see FIG. 12. This may be used as a warning to the user to reapply vacuum to the enclosure 100 and restore the vacuum state. Even with loss of vacuum, sterility will still be maintained as the air will leak inside the sterile enclosure 100 and not from within the sterile enclosure to the outside space surrounding thereof. More importantly, it draws user's attention to closely inspect the sterile enclosure 100 and the device 50 inside for any sign of leakage of any liquid material into the space inside the sterile enclosure 100. User may decide to withdraw the sterile enclosure 100 from the operating field when there is a minimal visible leakage to prevent any potential damage to the device 50, when it is not waterproof. Any larger amount of leakage will indicate higher chance of contamination and putting sterility of the operating field at risk.

In embodiments, an alternative way to monitor vacuum would be to operate the device to continuously monitor surrounding pressure to assure that initial level of vacuum is maintained throughout the use of the device. In case the vacuum is diminished or lost altogether, the device may be programmed to sound an alarm. A dedicated smartphone app to perform this functionality may be developed and activated during use within a sterile field.

In embodiments, a method of bringing a non-sterile hand-held electronic device into a sterile field may include the following steps:

a. providing a sterile enclosure comprising a rigid base, a rigid frame, an air evacuation port, and a device holder configured for resting of the hand-held device therein, b. positioning the hand-held device onto the device holder, c. engaging the device holder with the base while the hand-held device is held together with the device holder, d. lowering the device holder and the hand-held device into the base, e. sealingly attaching the frame to the base forming an internal sealed space therein, f. evacuating air from the internal sealed space, and
g. bringing the sterile enclosure with the hand-held device inside thereof into the sterile field.

The method steps (b), (c), (d) may be performed by a first non-sterile person, whereas steps (e), (f), (g) may be performed by a second sterile person.

When the sterile enclosure further includes a sterility monitor as described above, the step (g) may also include monitoring sterility while the hand-held device remains in the sterile field.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A sterile enclosure for enclosing a hand-held electronic device therein, said sterile enclosure comprising:
    a rigid base shaped to have a lower sealing ledge and a depression sized to accept said hand-held electronic device therein,
    a rigid frame shaped to have an upper sealing ledge and containing a flexible transparent window within said upper sealing edge,
    wherein when assembled together, said base and said frame defining in internal sealed space of said sterile enclosure when said upper sealing ledge is sealingly attached to said lower sealing ledge,
    an air evacuation port comprising a one-way valve, said air evacuation port configured to evacuate air from said internal sealed space, and
    a device holder configured for resting of said hand-held device therein, said device holder comprising an engagement portion for attaching thereof to said base,
    a sterility indicator configured to indicate a loss in vacuum inside said internal sealed space without allowing air leakage therein, wherein said sterility indicator comprises an elastic collapsible chamber open to said internal space of the sterile enclosure and configured to shorten from an exposed position to a hidden position upon evacuation of air from said internal space of said sterile enclosure,
    whereby attaching said device holder containing said hand-held device thereon to said base prior to assembly of said base with said frame reduces a risk of contamination of said sterile enclosure.

2. The sterile enclosure as in claim 1, wherein said device holder further comprising a hinge portion for lowering said hand-held device into said depression of said base after attaching of said device holder to said base.

3. The sterile device as in claim 1, wherein said flexible transparent window is sized to cover a user interface portion of said hand-held device.

4. The sterile enclosure as in claim 1 further comprising an internally sealed electrical conduit sealingly routed therethrough and equipped with an internal electrical connector and an external electrical connector configured to extend electrical port connectors of said hand-held electronic device to outside said sterile enclosure without allowing air leakage into said internal sealed space after evacuating air therefrom.

5. The sterile enclosure as in claim 1, wherein either or both of said upper sealing ledge and said lower sealing ledge contains an adhesive layer covered with a removable masking tape.

6. The sterile enclosure as in claim 1, wherein said collapsible chamber comprises a bulb at a dead-end side thereof, said base further comprises a masking edge positioned to cover said bulb when said collapsible chamber is in a hidden position so as to confirm air evacuation from said internal space of said sterile enclosure when said bulb is not visible, said masking edge is further positioned to allow visibility of said bulb when said collapsible chamber is in said exposed position indicating no vacuum inside said internal space of said sterile enclosure and a breach of sterility thereof.

\* \* \* \* \*